United States Patent [19]

Nakajima

[11] 3,952,579

[45] Apr. 27, 1976

[54] AUTOMATIC BLOOD SEDIMENTATION RATE MEASURING DEVICE

[75] Inventor: Hiroyuki Nakajima, Ashiya, Japan

[73] Assignee: Konan Electric Co., Ltd., Nishinomiya, Japan

[22] Filed: July 1, 1974

[21] Appl. No.: 484,499

[30] Foreign Application Priority Data
June 30, 1973 Japan.............................. 48-74215

[52] U.S. Cl. ........................... 73/61.4; 346/33 ME; 356/39
[51] Int. Cl.² ....................................... G01N 15/04
[58] Field of Search ................................. 73/61–64; 356/39; 346/33 ME, 107 A, 107 R

[56] References Cited
UNITED STATES PATENTS

| | | | |
|---|---|---|---|
| 2,083,375 | 6/1937 | Hehlgans | 346/107 A |
| 2,725,782 | 12/1955 | Worley | 73/61.4 X |
| 3,261,256 | 7/1966 | Morton, Jr. | 73/61.4 |
| 3,288,019 | 11/1966 | Blumenfeld | 73/61.4 X |
| 3,422,443 | 1/1969 | Jansen | 356/39 X |
| 3,474,458 | 10/1969 | Standaart | 356/39 X |
| 3,604,924 | 9/1971 | Standaart | 356/39 X |
| 3,631,513 | 12/1971 | Fotsch et al. | 356/39 X |

Primary Examiner—James J. Gill
Assistant Examiner—Joseph W. Roskos
Attorney, Agent, or Firm—Sughrue, Rothwell, Mion, Zinn & Macpeak

[57] ABSTRACT

In a device for measuring blood sedimentation rate automatically, a light-sensitive paper sheet is disposed so as to be movable relative to a blood sedimentation measuring tube, such as Westergren tube; a slit is provided between the light-sensitive paper and the measuring tube; and lamp means are provided on one side of the measuring tube opposite to the slit. Thus, the shade of the sedimented red blood corpuscles in the measuring tube formed as the light pulses from the lamp means passes through the measuring tube is projected on the light-sensitive paper through the slit with the feed of the paper and light pulses occurring in exact synchronism, and the rate of the blood sedimentation can be automatically recorded on the paper.

13 Claims, 3 Drawing Figures

AUTOMATIC BLOOD SEDIMENTATION RATE MEASURING DEVICE

BACKGROUND OF THE INVENTION

This invention relates generally to blood sedimentation measuring techniques, and more particularly to a device adapted to record any variation in time of the blood sedimentation automatically on a sheet of light-sensitive paper.

Heretofore, the sedimentation rate of red blood corpuscles has been measured through the Westergren method or the Landsberg method. In accordance with the Westergren method, 0.4 ml of 3.8% sodium citrate solution is prepared beforehand in an injector, and then 1.6 ml of venous blood is taken into the injector so that altogether 2.0 ml of blood-sodium citrate mixture is obtained therein.

The mixture is then replaced in a Westergren tube which is thereafter held vertically, and the rate of sedimentation of red blood corpuscles is read manually by the aid of a scale graduated thereon at times of 30 minutes, 1 hour, and 2 hours after the initiation of the measurement.

However, the above described reading operation at accurate times of 30 minutes, 1 hour, and 2 hours after the initiation of the measuring operation is found to be no easy job, particularly in a large hospital or the like wherein a great number of blood sedimentation tests are carried out for blood taken at arbitrary times.

SUMMARY OF THE INVENTION

With the above described difficulty in view, a primary object of the present invention is to provide an automatic blood sedimentation rate measuring device which is of a simple construction and economical in manufacture.

Another object of the invention is to provide an automatic blood sedimentation rate measuring device which provide reliable test results.

Still another object of the invention is to provide an automatic blood sedimentation rate measuring device wherein, for instance, a Westergren tube can be freely detachably inserted, and the blood sedimentation therein can be read out without fail.

A further object of the invention is to provide an automatic blood sedimentation rate measuring device whereby the burden of those engaging in the blood sedimentation tests can be substantially reduced and the control of the testing operation is facilitated.

The automatic blood sedimentation rate measuring device according to the present invention comprises a light-sensitive paper sheet disposed so as to be movable relative to a blood sedimentation measuring tube, such as a Westergren tube, a slit provided between the light-sensitive paper and the blood sedimentation measuring tube, and lamp means provided on one side of the measuring tube opposite to the slit, whereby the shade of the sedimented red blood corpuscles in the measuring tube formed as the light from the lamp means passes through the measuring tube is projected through the slit on the light-sensitive paper, and the rate of the blood sedimentation can be automatically recorded with reference to time on the paper.

The invention will be more clearly understood from the following detailed description of the invention when read in conjunction with the accompanying drawings.

DETAILED DESCRIPTION OF THE INVENTION

Figure 1:
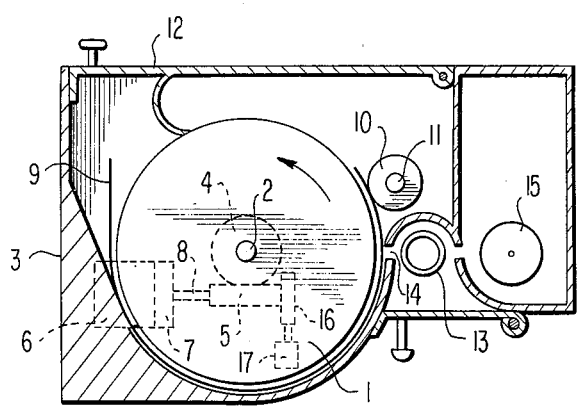
FIG. 1 is a plan view, partly in section, of an automatic blood sedimentation rate measuring device according to the present invention.
Figure 2:
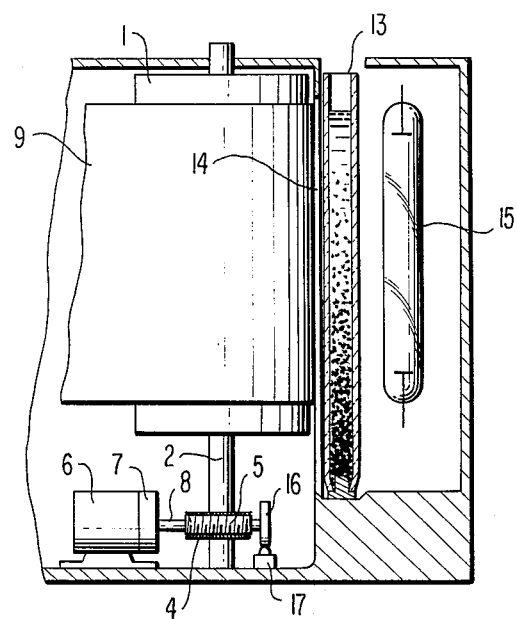
FIG. 2 is a fragmental, elevational view showing one part of the automatic blood sedimentation rate measuring device of FIG. 1.

Referring now to FIGS. 1 and 2, there is indicated a paper sheet feeding drum 1 rotatably supported in a casing 3 through a vertically disposed central shaft 2. A worm wheel 4 meshing with a worm 5 is securely mounted on the lower end portion of the shaft 2. The worm 5 is adapted to be coupled with an output shaft 8 of a reduction gear mechanism 7 which is in turn driven by an electric motor 6. It should be noted that the worm 5 may be driven by the reduction gear mechanism 7 at a constant rotational speed or may be driven in an intermittent manner.

In the case where the longest required measuring time of the blood sedimentation is assumed to be two hours and the circumference of the paper feeding drum 1 is assumed to be equivalent to the length of a light-sensitive paper sheet 9, the speed reduction ratio of the reduction gear mechanism 7 and the rotating speed of the electric motor 6 are so selected that the paper feeding drum 1 is rotated by one complete turn within about 2 hours and 30 minutes. A roller 10, having a central shaft 11 extending vertically, is freely rotatably supported in the casing 3 at a position hereinafter described so that the roller 10 is urged lightly onto the peripheral surface of the paper feeding drum 1.

The light-sensitive paper sheet 9 is first introduced between an inner wall of the casing 3 and the outer surface of the paper feeding drum 1 as indicated in FIG. 1. Along with the rotation of the paper feeding drum 1, the light-sensitive paper sheet 9 is advanced along the circumference of the paper sheet feeding drum 1 so that the leading edge of the paper 9 is finally held between the roller 10 and the outer surface of the paper feeding drum 1. The casing 3 is of a light-shielding construction, whereby when a door 12 is closed, no intrusion of outside light into the casing 3 occurs.

A blood sedimentation rate measuring tube 13 of, for instance, of the Westergren type, is inserted in the casing 3 in the proximity of the roller 10 located on the side of the paper feeding drum 1 opposite to the entrance portion for the light-sensitive paper sheet 9, and is detachably held vertically in that position. Between the Westergren tube 13 and the light-sensitive paper 9 wound on the circumference of the paper sheet feeding drum 1, a vertically extending slit 14 is provided through a part of the structure of the casing 3. The vertical length of the slit 14 is so selected that it is substantially equal to the width of the light-sensitive paper 9 wound around the circumference of the paper sheet feeding drum 1. The width of the light-sensitive paper sheet 9, measured along a generatrix of the drum 1, is in turn selected to be slightly greater than 150 mm which corresponds to a maximum expected height of the supernatant plasmatic portion in the Westergren tube 13.

The supporting means for the Westergren tube 13 is so designed that the tube 13 is held in its position keeping the upper end of the blood mixture contained in the Westergren tube 13 slightly lower than the upper edge of the light-sensitive paper 9. A lamp or a flashlight bulb 15 is provided in the casing 3 at a position opposite to the light-sensitive paper 9 with respect to the Westergren tube 13. The casing 3 is so constructed that the light-sensitive paper sheet 9 is not exposed to any other light than that from the lamp or the flashlight bulb 15. When the lamp or bulb 15 is lit, the light rays from the lamp or bulb 15 are passed through the Westergren tube 13 and the slit 14, and images in the form of shades of the sedimented red blood corpuscles and the upper supernatant plasmatic portion are thereby projected on the light-sensitive paper sheet 9. The sensitivity of the light-sensitive paper sheet 9 and the intensity of the light rays generated from the lamp or bulb 15 are so selected that the light passing through the supernatant plasmatic portion of the Westergren tube 13 can cause sufficient exposure of the light-sensitive paper 9 but the sedimented red blood corpuscle portion of the same tube cannot cause sufficient exposure to the light-sensitive paper 9.

The lamp or flashlight bulb (hereinafter termed lamp means) 15 may be of any desired type such as a tungsten bulb, the intensity of light generated therefrom can be easily regulated and a clear image can be thereby produced on the light-sensitive paper sheet 9. In successfully executed examples, so-called strobolamp of photographical use and containing xenon gas was used in a manner of intermittent lighting. The lighting period of this strobo-lamp was approximately 1/3000 sec. In these examples, the circumferential length of the light-sensitive paper wound around the drum 1 was selected to 100 mm, the narrow gap of the slit 14 was selected to 1 mm, and the lamp was lit three times per minute, thus permitting to draw automatically, a clear blood sedimentation rate-time curve on the light-sensitive paper 9. The light-sensitive paper was of a kind used for electromagnetic oscillographs.

As for the lighting signal source for the lamp means, any of the conventional devices suited for the purpose can be used. In the example illustrated in FIGS. 1 and 2, however, a cam 16 is interlinked with the worm 5, and the lighting signal is obtained from a microswitch 17 operated by the cam 16 at fixed intervals, thus maintaining exact synchronism therebetween.

Figure 3:
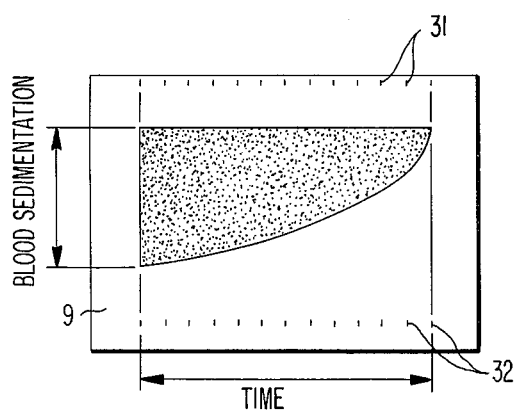
FIG. 3 is a graphical representation of the blood sedimentation relative to time.

The device of the above description utilizes the difference in transparency between the sedimented red blood corpuscle portion and the supernatant plasmatic portion in a dexterous manner, and by projecting the shade of the Westergren tube 13 through the slit 14 intermittently on the light-sensitive paper 9 moving relative to the same tube 13, the sedimented rate of the blood can be recorded continuously on the light-sensitive paper sheet 9. Upon taking out the paper after a predetermined period, a pattern delineated by color difference caused by the different transparency can be obtained on the light-sensitive paper sheet 9 as shown in FIG. 3 although in some kinds of paper, the pattern can be obtained after development. In the above described graphical representation, time is represented by the abscissa, the unit length of which is determined by the rotating speed of the paper sheet feeding drum 1. In the graphical representation, height of blood sedimentation after a predetermined time can be found easily.

In the graph shown in FIG. 3, those indicated at 31 and 32 are time marks which may be obtained in any suitable manner. For instance, the roller 10 may be made into a hollow construction, allowing to the inclusion of a small lamp or the introduction of outside light into the hollow space. A plurality of slits (not shown) are further provided within the peripheral wall of the roller 10 at positions corresponding to the time marks 31 and 32 and with a constant spacing between each other. Thus, when the roller 10 is rotated in contact with the light-sensitive paper sheet wound on the paper sheet feeding drum 1, the time marks 31 and 32 can be formed on the light-sensitive paper 9.

The blood sedimentation rate measuring device according to the present invention can be of a simple construction as described above, and the operation thereof is highly reliable regardless of its low manufacturing cost. Furthermore, the device according to the invention can provide automatic measurement of the sedimentation rate of the red blood corpuscles without fail, and hence the aforementioned difficulty in the conventional methods can be substantially eliminated.

Although the invention has been described with reference to a preferred embodiment thereof, it would be apparent to those skilled in the art that various modifications and alterations can be carried out without departing the spirit and scope of the present invention. For instance, when a green filter is further provided between the Westergren tube 13 and the lamp means 15 or between the Westergren tube 13 and the light-sensitive paper 9 at a position adjacent the slit 14, the difference between the shade of the sedimental red blood corpuscle portion and the shade of the supernatant plasmatic portion can be increasingly clarified. Furthermore, the lamp means which have been described as an intermittently lit strobo-lamp may be a continuously lamp lit, or the paper feeding drum 1 which has been described as a continuously moving drum may be changed to an intermittently rotated drum. In addition, the blood sedimentation rate measuring tube which has been exemplarily described as Westergren tube may be of any other suitable type for measuring blood sedimentation rate. Most of the tubes used for measuring blood sedimentation rate differ only in the kind of the reagent used therein and the size of the tubes.

What is claimed is:

1. An automatic blood sedimentation rate measuring device for photographic recording the blood sedimentation rate on individual, light-sensitive paper sheets, said device comprising:
    a light-proof casing,
    a cylindrical drum,
    means for mounting said cylindrical drum for rotation within said light-proof casing about a vertical axis,
    said light-proof casing including a curved wall portion conforming to a portion of the periphery of said drum and being spaced slightly therefrom to define a narrow gap for receiving said light-sensitive paper sheet during rotation of said drum,
    an elongated blood sedimentation measuring tube mounted within said casing and extending vertically parallel to the axis of said drum,
    said light-proof casing including means defining a light barrier between said tube and said paper sheet, a vertical slit within said barrier and parallel to the axis of said tube, a lamp provided on the side of the blood sedimentation measuring tube opposite said slit, motor means for moving said drum to cause light-sensitive paper sheet to move with the drum periphery across said slit, means for pressing said paper sheet to said drum periphery during drum rotation, switch means for controlling energization of said lamp, and means driven by said motor means for periodically operating said switch means to synchronize lamp energization and production of light pulses with drum movement;

whereby, the shade of the sedimented red blood corpuscles in the measuring tube formed as the light from the lamp means passes through the measuring tube is projected through the slit onto the light-sensitive paper sheet and the rate of the blood sedimentation is automatically recorded with time on the moving paper sheet.

2. A device as set forth in claim 1, wherein said motor means drives said drum at a constant rate about its axis.

3. A device as set forth in claim 1, wherein said motor means drives said drum intermittently about its axis.

4. A device as set forth in claim 1, wherein said drum is rotated in one complete turn in approximately two and a half hours.

5. A device as set forth in claim 1, wherein said means for pressing said paper sheet to said drum periphery comprises a roller of hollow construction mounted for free rotation about its axis, said roller is lightly urged against the light-sensitive paper wound around said drum, a plurality of slits are provided within the peripheral wall of said roller equally spaced apart, lighting means is provided interior of said hollow roller, and said roller is rotated in accordance with the rotation of said drum, whereby; time marks are provided on said light-sensitive paper.

6. A device as set forth in claim 1, wherein the width of said light-sensitive paper measured along the length of said blood sedimentation measuring tube is selected to be greater than the maximum expected height of the supernatant plasmatic portion of said blood sedimentation measuring tube.

7. A device as set forth in claim 1, wherein said blood sedimentation measuring tube is of Westergren type.

8. A device as set forth in claim 1, wherein said blood sedimentation measuring tube is of Landsberg type.

9. A device as set forth in claim 1, wherein the length of said slit is selected to be substantially equal to the width of said light-sensitive paper measured along the length of said blood sedimentation measuring tube.

10. A device as set forth in claim 1, wherein said lamp means is selected to be a tungsten lamp, the brightness of which is regulated in accordance with the sensitivity and the moving speed of said light-sensitive paper.

11. A device as set forth in claim 1, wherein said lamp means is selected to be a strobo-lamp with intermittent lighting periods of approximately 1/3000 sec.

12. A device as set forth in claim 1, wherein said light-sensitive paper sheet is of a type used for electromagnetic oscillographs.

13. A device as set forth in claim 1, wherein a green filter is further inserted between the blood sedimentation measuring tube and said light-sensitive paper sheet.

* * * * *